United States Patent
Bodhuri et al.

(10) Patent No.: US 10,556,887 B2
(45) Date of Patent: Feb. 11, 2020

(54) PROCESSES FOR THE PREPARATION OF VELIPARIB AND INTERMEDIATES THEREOF

(71) Applicant: Apotex Inc., Toronto (CA)

(72) Inventors: Prabhudas Bodhuri, Torrance, CA (US); Kaarina K. Milnes, Cambridge (CA); Melanie R. A. Green, Milton (CA); Gamini Weeratunga, Ancaster (CA); Boris Gorin, Oakville (CA)

(73) Assignee: Apotex Inc., Toronto, Ontario (CA)

( * ) Notice: Subject to any disclaimer, the term of this patent is extended or adjusted under 35 U.S.C. 154(b) by 0 days.

(21) Appl. No.: 16/167,882

(22) Filed: Oct. 23, 2018

(65) Prior Publication Data

US 2019/0119257 A1    Apr. 25, 2019

Related U.S. Application Data

(60) Provisional application No. 62/576,125, filed on Oct. 24, 2017.

(51) Int. Cl.
*C07D 403/04* (2006.01)
*C07D 207/16* (2006.01)

(52) U.S. Cl.
CPC ......... *C07D 403/04* (2013.01); *C07D 207/16* (2013.01)

(58) Field of Classification Search
None
See application file for complete search history.

(56) References Cited

U.S. PATENT DOCUMENTS 7,550,603 B2    6/2009    Zhu et al.

FOREIGN PATENT DOCUMENTS

| CN | 103755595 A | 4/2014 |
|---|---|---|
| CN | 106432195 A | 2/2017 |
| WO | 2006110816 A2 | 10/2006 |
| WO | 2011012622 A1 | 2/2011 |
| WO | 2015139656 A1 | 9/2015 |

OTHER PUBLICATIONS

Beck et al., "Synthesis of (S)-2-Methylproline: A General Method for the Preparation of α-Branched Amino Acids", Organic Syntheses, 1995, p. 62, vol. 72.

Ich Harmonised Guideline, "Impurities: Guideline for Residual Solvents Q3C(R6)", 2016, Version Step 4.

Lu et al., "Improved synthesis of PARP antagonist veliparib", Chinese Journal of Medicinal Chemistry, 2013, pp. 476-479, vol. 23, No. 6. (Reference is relevant for the reasons stated in the Specification/English-language Abstract attached).

Overberger et al., "Synthesis and Solution Properties of Poly(2-methylproline)", Journal of Polymer Science: Polymer Chemistry Edition, 1977, pp. 1413-1421, vol. 15.

Penning et al., "Discovery of the Poly(ADP-ribose) Polymerase (PARP) Inhibitor 2-[(R)-2-methylpyrrolidin-2-yl]-1H-benzimidazole-4-carboxamide (ABT-888) for the Treatment of Cancer", Journal of Medicinal Chemistry, 2009, pp. 514-523, vol. 52.

*Primary Examiner* — Samantha L Shterengarts
(74) *Attorney, Agent, or Firm* — The Webb Law firm

(57) ABSTRACT

The present invention provides processes for the preparation of Veliparib (1), as well as intermediates useful in the preparation thereof. In particular, processes are provided for the production of the compound of Formula (3), or a salt thereof, and cyclization to afford Veliparib (1).

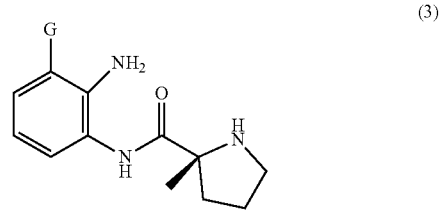

20 Claims, No Drawings

PROCESSES FOR THE PREPARATION OF VELIPARIB AND INTERMEDIATES THEREOF

CROSS-REFERENCE TO RELATED APPLICATION

This application claims the benefit of U.S. Provisional Patent Application No. 62/576,125, filed Oct. 24, 2017, the disclosure of which is hereby incorporated in its entirety by reference.

TECHNICAL FIELD

The present invention relates to processes for the preparation of Veliparib (1) and intermediates used in the preparation thereof.

BACKGROUND

Veliparib (1), or 2-[(2R)-2-methyl-2-pyrrolidinyl]-1H-benzimidazole-4-carboxamide, is a poly(ADP-ribose) polymerase (PARP) inhibitor, and is undergoing evaluation in patients with non-small cell lung cancer (NSCLC), breast cancer and ovarian cancer in the United States. Veliparib (1) has the following structural formula:

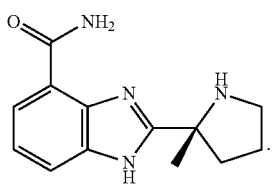

(1)

Scheme 1 depicts a method of preparing Veliparib (1) that is described in WO 2006/110816 A2 and in Penning, T. D. et al. *J. Med. Chem.* 2009, 52, 514. In this method, carbonyldiimidazole (CDI)-mediated coupling of racemic carbobenzyloxy (Cbz)-protected 2-methylproline (A) with diamine dihydrochloride (B) provides racemic amide (C), which undergoes ring formation upon treatment in refluxing acetic acid to afford racemic benzimidazole (D). Following separation of the (R)- and (S)-enantiomers of racemic benzimidazole (D) by chiral HPLC, the resulting (R)-(D) enantiomer is subjected to deprotection under hydrogenolysis conditions to provide Veliparib (1).

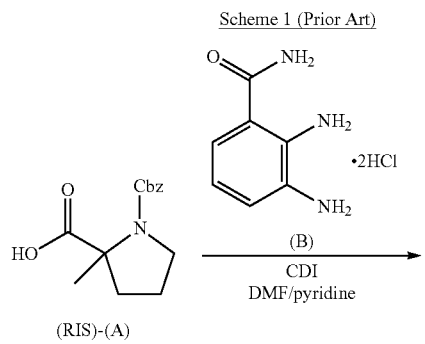

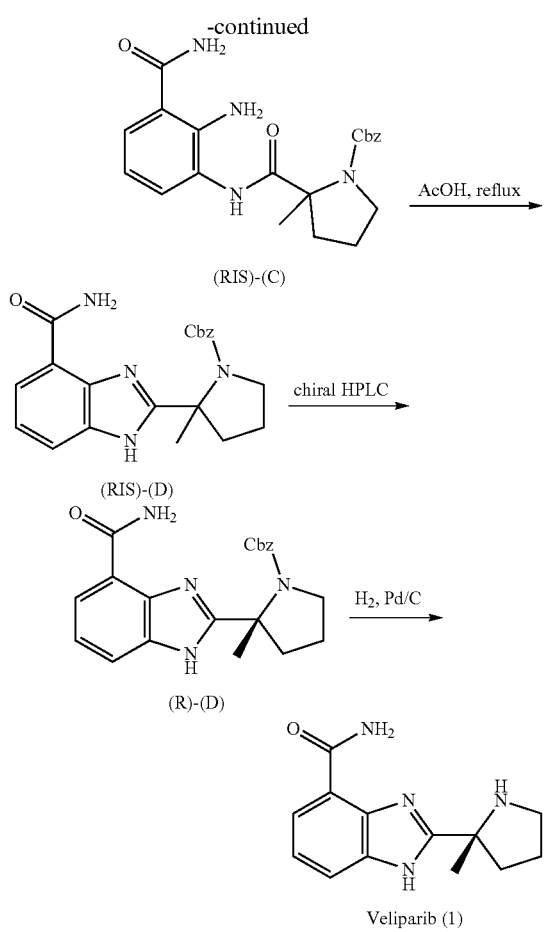

However, the process described in WO 2006/110816 A2 suffers from a number of limitations that reduce its usefulness for large scale manufacturing. For example, the coupling between (Cbz)-protected 2-methylproline (A) and diamine dihydrochloride (B) utilizes a large excess of pyridine, a toxic and odorous solvent. Furthermore, the procedure requires separation of the (R)- and (S)-enantiomers of benzimidazole (D) by chiral HPLC, which not only results in a loss of 50% of the material at an advanced stage of the overall synthesis, also involves use of specialised and costly chiral chromatography columns and equipment that is prohibitive for large scale production. Finally, removal of the Cbz protecting group in the final step by palladium-catalysed hydrogenolysis is disadvantageous because it limits the number of further opportunities to purge the residual transition metal palladium, which must be controlled to very low levels in pharmaceutical products.

A similar process for the preparation of Veliparib (1) is described in Lu, T-X. et al. *Chinese Journal of Medicinal Chemistry* 2013, 23(6), 476, wherein the use of chiral chromatography to separate late-stage intermediates is replaced by the use of the (R)-enantiomer of 2-methylproline derivative as a starting material. Other approaches to the preparation of Veliparib (1) and analogous compounds, such as those reported in CN 103755595 A and WO 2015139656 A1, also utilize chiral starting materials. However, these methods fail to avoid other problematic aspects of the overall synthesis, such as use of palladium-catalysed hydrogenolysis in the final step to remove the Cbz protecting group, and use of reagents/solvents which are questionable for large scale production, such as excessive pyridine or potentially explosive benzotriazole coupling agents, such as HATU (1-[bis(dimethylamino)methylene]-1H-1,2,3-triazolo[4,5-b]pyridinium 3-oxid hexafluorophosphate). A further route to Veliparib (1), reported in CN 106432195 A, avoids the final hydrogenolysis deprotection by employing t-butoxycarbonyl (BOC) as a protecting group, which is removed following benzimidazole formation by treatment with aqueous acetic acid. However, the intermediates used in this process are prepared by the methods of WO 2006/110816 A2, and therefore remain associated with the problems discussed above.

In each of the above cited methods for the preparation of Veliparib (1), the racemic or chiral N-protected 2-methylproline (A) is activated for coupling with diamine (B) using a coupling agent such as CDI or HATU. Another method known for the activation of α-amino carboxylates like 2-methylproline (A) for use in coupling reactions involves formation of an N-carboxyanhydride (NCA) derivative. In Overberger, C. G. et al *J. Polym. Sci. Polym. Chem. Ed.* 1977, 15, 1413, a procedure is disclosed for the preparation of the NCA derivative (E) of (R)-2-methyl proline having the following formula:

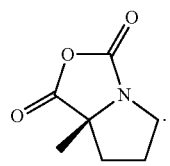

(E)

The procedure provided in Overberger et al. involves treatment of N-carbobenzoxy-(R)-2-methylproline with phosphorous pentachloride followed by removal of persistent phosphorous impurities by repeated recrystallization from carbon tetrachloride/n-pentane to afford the NCA derivative in only 25% yield. The use of carbon tetrachloride, classified by ICH (International Conference on Harmonisation of Technical Requirements for Pharmaceuticals for Human Use) Guidance Q3C (R6) as Class 1 (solvents that should not be employed in the manufacture of drug substances, excipients, and drug products because of their unacceptable toxicity or their deleterious environmental effect), the necessity for repeated recrystallizations, and the low yield obtained are obvious disadvantages of this approach that limit its widespread use in commercial processes.

Accordingly, a need exists for improved processes for the preparation of Veliparib (1), and the intermediates used in such preparations, that are more amenable to scale-up and use on a commercial scale.

SUMMARY OF THE INVENTION

The present invention provides improved processes for the preparation of Veliparib (1), as depicted in Scheme 2. As well, the present invention provides new intermediates that can be used in the preparation of Veliparib (1), and processes for their preparation.

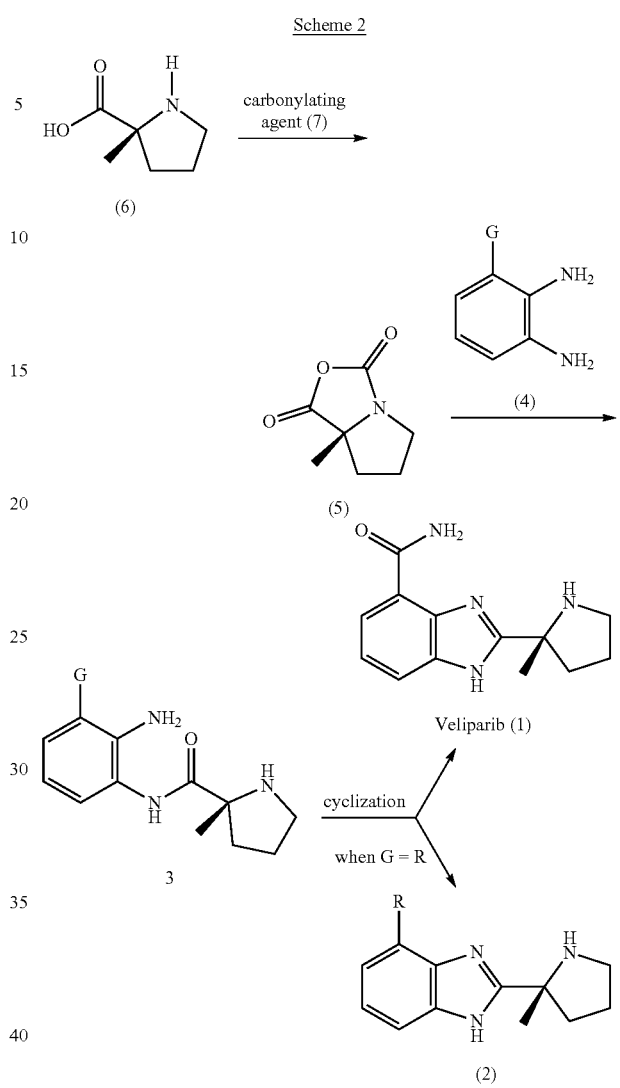

wherein
G is $CONH_2$ or R;
R is $CO_2R^1$ or CN; and
$R^1$ is selected from the group consisting of H, an aliphatic group, a substituted aliphatic group, aryl, substituted aryl, arylalkyl and substituted arylalkyl.

As shown in Scheme 2, Veliparib (1) may be prepared according to the process of the present invention by reacting the compound of Formula (6) with a carbonylating agent to provide the compound of Formula (5). Coupling of the compound of Formula (5) with a diamine of Formula (4) provides the compound of Formula (3), which undergoes cyclization to provide Veliparib (1), either directly, or, when G is R, conversion of the substituent R of Formula (2) to $CONH_2$. Conversion of the compound of Formula (6) to the corresponding NCA derivative of Formula (5) provides two advantages. First, the carboxylic acid group of the compound of Formula (6) is activated for coupling with the diamine of Formula (4). Second, due to the loss of the NCA portion of the compound of Formula (5) during this subsequent coupling step, the compound of Formula (3) does not bear a protecting group (for example, the Cbz group in the processes described in the prior art above) that must be removed in a later step.

As a result of the dual activation/deprotection step utilized by the process of the present invention, the need for a discrete transition metal-catalysed deprotection operation following cyclization in the final step of the prior art syntheses described above is eliminated. Surprisingly, despite the absence of a protecting group on the compound of Formula (3), the subsequent cyclization proceeds cleanly to deliver Veliparib (1) or the compound of Formula (2), depending on the nature of the substituent G. This is particularly surprising given the consistent use in known processes for the preparation of Veliparib (1), of a protecting group on the ring nitrogen of analogues of the compound of Formula (3). Accordingly, the present invention provides processes for the preparation of Veliparib (1) and intermediates thereof, which are efficient and avoid the use of hazardous substances such as carbon tetrachloride, pyridine, benzotriazoles, and transition metals.

In a preferred embodiment of the process shown in Scheme 2, a high yielding sequence is provided involving coupling and concomitant cyclization, wherein the NCA derivative of Formula (5) reacts with the compound of Formula (4) in the presence of an acid, followed by spontaneous cyclization of the product of Formula (3) to afford either the compound of Formula (2) or Veliparib (1), without isolation of the intermediate products. In this preferred embodiment of the present invention, Veliparib (1) can be produced from the compound of Formula (6) in as few as two steps.

Further advantages are provided by the processes of the present invention in the provision of novel crystalline intermediate (3), which offers further opportunities for isolation and purification, if desired.

Accordingly, in a first aspect of the present invention, there is provided a process for preparing Veliparib (1) or a salt thereof, comprising:
  (i) cyclizing, in the presence of an acid (A1), a compound of Formula (3), wherein G is $CONH_2$ or R, R is $CO_2R^1$ or ON, and $R^1$ is selected from the group consisting of H, an aliphatic group, a substituted aliphatic group, aryl, substituted aryl, arylalkyl and substituted arylalkyl, to provide either Veliparib (1) when G is $CONH_2$, or a compound of Formula (2) when G is R; and
  (ii) when G is R, converting the compound of Formula (2) to Veliparib (1).

In a preferred embodiment of the first aspect, G is $CONH_2$. In a further preferred embodiment of the first aspect, G is R, R is $CO_2R^1$, and $R^1$ is H. In a further preferred embodiment of the first aspect, G is R, R is $CO_2R^1$, and $R^1$ is an aliphatic group. In this embodiment, $R^1$ is preferably C1-C6 alkyl, and more preferably methyl. In a further preferred embodiment of the first aspect, G is R, and R is CN.

In another preferred embodiment of the first aspect, in step (ii), converting the compound of Formula (2), wherein G is $CO_2H$, to Veliparib (1) comprises treating the compound of Formula (2) with a chlorinating agent to activate the carboxylic acid, followed by treating the activated carboxylic acid with a source of ammonia. Preferably, the chlorinating agent is selected from the group consisting of thionyl chloride and oxalyl chloride, and the source of ammonia is selected from the group consisting of ammonia gas, ammonium hydroxide and methanolic ammonia.

In another preferred embodiment of the first aspect, in step (ii), converting the compound of Formula (2), wherein G is $CO_2R^1$ and $R^1$ is an aliphatic group, to Veliparib (1) comprises treating the compound of Formula (2) with a source of ammonia. Preferably, the source of ammonia is selected from the group consisting of ammonia gas, ammonium hydroxide and a solution of ammonia in methanol solvent.

In another preferred embodiment of the first aspect, in step (ii), converting the compound of Formula (2), wherein G is CN, to Veliparib (1) comprises hydrolyzing the compound of Formula (2) with an acid (A2) or a base (B3). Preferably, the conversion comprises hydrolysis with base (B3) which is potassium t-butoxide.

Preferably, in the process of the first aspect of the invention, acid (A1) is a substantially anhydrous acid selected from the group consisting of carboxylic acids, sulfonic acids and mineral acids. Most preferably, acid (A1) is acetic acid. When acid (A1) is acetic acid and G in the compound of Formula (3) is $CONH_2$, Veliparib (1) is preferably provided as a diacetic acid salt.

In a second aspect of the present invention, there is provided a process for preparing Veliparib (1), or a salt thereof, from a compound of Formula (2), or a salt thereof, wherein R is $CO_2R^1$ or ON, and $R^1$ is selected from the group consisting of H, an aliphatic group, a substituted aliphatic group, aryl, substituted aryl, arylalkyl and substituted arylalkyl, the process comprising:
  (i) when R is $CO_2R^1$ and $R^1$ is H, treating the compound of Formula (2) with a chlorinating agent to activate the carboxylic acid followed by amidating the activated carboxylic acid with a source of ammonia;
  (ii) when R is $CO_2R^1$ and $R^1$ is selected from the group consisting of an aliphatic group, a substituted aliphatic group, aryl, substituted aryl, arylalkyl and substituted arylalkyl, amidating the compound of Formula (2) with a source of ammonia; or
  (iii) when R is CN, hydrolyzing the compound of Formula (2) in the presence of an acid (A2) or a base (B3).

In a preferred embodiment of the second aspect, the process for preparing Veliparib (1) comprises step (ii), and in the compound of Formula (2), R is $CO_2R^1$ and $R^1$ is C1-C6 alkyl. In a further preferred embodiment, the ammonia source is selected from the group consisting of ammonia gas, ammonium hydroxide and methanolic ammonia. Most preferably, the ammonia source is methanolic ammonia.

In a third aspect of the invention, there is provided a process for preparing a compound of Formula (3), or a salt thereof, comprising coupling, in the presence of a solvent (S2), of the compound of Formula (5) with a compound of Formula (4), or a salt thereof, wherein, in the compound of Formula (4), G is $CONH_2$ or R, R is $CO_2R^1$ or ON, and $R^1$ is selected from the group consisting of H, an aliphatic group, a substituted aliphatic group, aryl, substituted aryl, arylalkyl and substituted arylalkyl.

In a preferred embodiment of the third aspect, G in the compound of Formula (3) and Formula (4) is $CONH_2$. In another preferred embodiment of the third aspect, solvent (S2) is selected from the group consisting of 1,4-dioxane, tetrahydrofuran, N,N-dimethylformamide and N-methyl-2-pyrrolidone. In another preferred embodiment of the third aspect, the coupling is conducted at a temperature of at least about 50° C. In another preferred embodiment of the third aspect, the coupling is conducted in the presence of a base (B2-B) that is selected from the group consisting of 4-(dimethylamino)pyridine and 1-methylimidazole.

Preferably, when practicing the process of the present invention according to the first aspect, the compound of Formula (3) is prepared according to the process of the third aspect of the invention. More preferably, when the coupling of the compound of Formula (4) and the compound of Formula (5) is conducted in the presence of an acid (A1), wherein acid (A1) is substantially anhydrous, the compound of Formula (3) undergoes cyclization to provide the compound of Formula (2) or Veliparib (1) without isolating the compound of Formula (3). More preferably, acid (A1) is selected from the group consisting of formic acid, acetic acid, p-toluene sulfonic acid, sulfuric acid and hydrochloric acid. Most preferably, acid (A1) is acetic acid.

In a fourth aspect of the present invention, there is provided a process for preparing the compound of Formula (5), comprising reacting, in the presence of a solvent (S1), the compound of Formula (6) with a carbonylating agent.

In a preferred embodiment of the fourth aspect, the carbonylating agent is a compound of Formula (7):

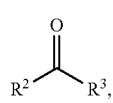

(7)

wherein $R^2$ and $R^3$ are independently selected from the group consisting of X, $OR^4$, $OCX_3$, imidazol-1-yl, 2-methylimidazol-1-yl and N-hydroxysuccinimidyl; X is halide; and $R^4$ is selected from the group consisting of alkyl, substituted alkyl, aryl and substituted aryl. More preferably, the carbonylating agent is triphosgene or carbonyldiimidazole. Most preferably, the carbonylating agent is carbonyldiimidazole.

In a further preferred embodiment of the fourth aspect, the reaction is conducted in the presence of imidazole hydrochloride. In another preferred embodiment of the fourth aspect, solvent (S1) is selected from the group consisting of halogenated hydrocarbons, alkyl esters, ethers, nitriles and formamides. More preferably, solvent (S1) is dichloromethane.

Preferably, when practicing the process of the present invention according to the third aspect, the compound of Formula (5) is prepared according to the process of the fourth aspect of the invention.

In a fifth aspect of the present invention, there is provided a compound of Formula (3), or a salt thereof, wherein G is $CONH_2$ or R; R is $CO_2R^1$ or CN; and $R^1$ is selected from the group consisting of H, an aliphatic group, a substituted aliphatic group, aryl, substituted aryl, arylalkyl and substituted arylalkyl. In a preferred embodiment of the fifth aspect, G is $CONH_2$ or $CO_2R^1$ and $R^1$ is C1-C6 alkyl.

In another preferred embodiment of the fifth aspect, there is provided the compound having the Formula (3-A):

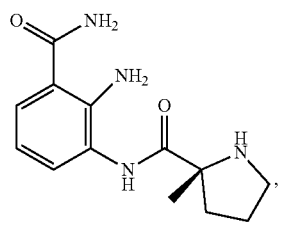

(3-A)

or a salt thereof.

In another preferred embodiment of the fifth aspect, there is provided the compound having the Formula (3-BA1):

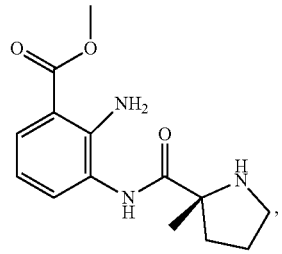

(3-BA1)

or a salt thereof.

In a sixth aspect of the present invention, there is provided a compound of Formula (2):

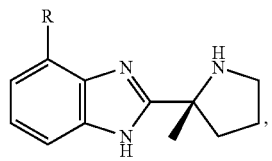

(2)

or a salt thereof, wherein R is $CO_2R^1$ or CN; and $R^1$ is selected from the group consisting of H, a C2-C10 aliphatic group, a C1-C10 substituted aliphatic group, aryl, substituted aryl, arylalkyl and substituted arylalkyl. In a preferred embodiment of the sixth aspect, R is $CO_2R^1$ and $R^1$ is C2-C6 alkyl.

In a seventh aspect of the present invention, there is provided the diacetic acid salt of Veliparib (1).

DETAILED DESCRIPTION

Development of the processes of the present invention followed from the discovery by the inventors that problems associated with the known processes for the preparation of Veliparib (1) could be overcome through the use of a novel dual activation/deprotection strategy to ultimately afford the compound of Formula (3), which, surprisingly, is capable of cyclizing to provide Veliparib (1) without the need for a protecting group on the ring nitrogen. In preferred embodiments, the novel dual activation/deprotection process of the present invention is followed by a cascading coupling and cyclization sequence, allowing for the production of Veliparib (1) in high yield in only two steps from the compound of Formula (6). Additionally, when G is $CO_2R^1$ or CN, a novel pathway to Veliparib (1), proceeding through a compound of Formula (2), is provided. This allows for a greater diversity of options in the compound of Formula (4) to be used.

Through the use of the process of the present invention, it is possible to avoid the use of hazardous substances that are employed in the known processes for the preparation of Veliparib (1) and intermediates thereof, such as carbon tetrachloride, pyridine, benzotriazoles and transition metals.

As used herein, the term "aliphatic", alone or as part of another substituent, means, unless otherwise stated, a straight chain, branched chain or cyclic hydrocarbon radical, or a combination thereof, which may be fully saturated, or mono- or polyunsaturated, and can include di- and multivalent radicals, having the number of carbon atoms designated. Examples of saturated hydrocarbon radicals include, but are not limited to, groups such as methyl, ethyl, n-propyl, iso-propyl, n-butyl, t-butyl, iso-butyl, sec-butyl, hexanyl, 2-methyl-2-hexanyl, cyclohexyl, 1-methylcyclohexyl, cyclopropylmethyl, and isomers of, for example, n-pentyl, n-hexyl, n-heptyl, n-octyl, and the like. Preferably, saturated hydrocarbon radicals have 1 to 4 carbons, and are selected from the group consisting of methyl, ethyl, n-propyl, iso-propyl, n-butyl, t-butyl, iso-butyl and sec-butyl. An unsaturated hydrocarbon radical is one having one or more double bonds or triple bonds. Preferred examples of unsaturated hydrocarbon radicals include, vinyl, 2-propenyl, crotyl, 2-isopentenyl, 2-(butadienyl), 2,4-pentadienyl, 3-(1,4-pentadienyl), norbornenyl, ethynyl, 1-propynyl, 2-propynyl, 3-butynyl, and the higher homologs and isomers.

As used herein, the term "alkyl", alone or as part of another substituent, means, unless otherwise stated, a straight or branched chain, saturated hydrocarbon radical having the number of carbon atoms designated (e.g., C1-C4 means one to four carbon atoms). When there is no indication of the number of carbon atoms in the alkyl, it is meant, unless otherwise indicated by context, that there are from 1 to 10 carbons. Preferred examples of saturated hydrocarbon groups include methyl, ethyl, n-propyl, iso-propyl, n-butyl, t-butyl, iso-butyl and sec-butyl.

As used herein, the term "aryl", alone or as part of another substituent, means, unless otherwise stated, a polyunsaturated, aromatic, hydrocarbon radical which can be a single ring or multiple rings (preferably from 1 to 3 rings) which are fused together or linked covalently having the number of carbon atoms designated. When there is no indication of the number of carbon atoms in the aryl, it is meant, unless otherwise indicated by context, that there are from 6 to 12 carbons. Preferred examples of aryl groups include phenyl, 1-naphthyl, 2-naphthyl and 4-biphenyl.

As used herein, the term "arylalkyl", alone or as part of another substituent, means, unless otherwise stated, an aryl substituent as defined herein attached through an alkyl radical to the parent structure. When there is no indication of the number of carbon atoms in the arylalkyl group, it is meant, unless otherwise indicated by context, that there are from 7 to 20 carbons. Preferred examples of arylalkyl groups include benzyl and phenethyl.

As used herein, the term "substituted" refers to the replacement of one or more hydrogen atoms with any one of a variety of substituents. A substituent may be a non-hydrogen atom or multiple atoms of which at least one is a non-hydrogen atom and one or more may or may not be hydrogen atoms. A substituted group (e.g., substituted —CH$_2$CH$_3$) may be fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.). Substituted compounds may comprise substituents selected from the group consisting of: R''', OR''', NR''R'', SR'', halogen, SiR'''R'''R''', OCOR''', COR'', CO$_2$R'', CONR''R'', NR''CO$_2$R''', NR''COR''', SOR''', SO$_2$R''', ON, NO$_2$ and CF$_3$. As used herein, each R'' may be selected, independently, from the group consisting of hydrogen, an aliphatic group, aryl and arylalkyl. As used herein, each R''' may be selected, independently, from the group consisting of an aliphatic group, aryl and arylalkyl. Preferred examples of substituent groups on substituted aryl groups include nitro, halide and alkyloxy.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

As used herein, "room temperature" refers to a temperature of 20-25° C.

As used herein, the terms "wt %" or "% w/w" refer to weight percent and is used to express weight solute/weight solution as a percentage.

As used herein, the term "about" means "close to" and that variation from the exact value that follows the term is within amounts that a person of skill in the art would understand to be reasonable. For example, when the term "about" is used with respect to temperature, a variation of ±5° C. is generally acceptable when carrying out the processes of the present invention. When used with respect to mole equivalents, a variation of ±0.1 moles is generally acceptable. When used with respect to volumes, a variation of 10% is generally acceptable.

As used herein, "substantially anhydrous", when used in relation to acid (A1) or acid (A2) refers to acids lacking adventitious water, typically corresponding with less than about 3 wt %, more preferably less than about 1 wt %, and most preferably less than about 0.5 wt %, water in the initial reaction system. Preferably, acids classified as being anhydrous are used, optionally with further treatment to minimize the water content, if desired.

In one embodiment of the present invention, Veliparib (1) and intermediates useful in the preparation thereof may be prepared by exemplary processes as set out in Scheme 2. Exemplary reagents and conditions for these reactions are disclosed herein.

In the processes described herein, the aliphatic group is preferably selected from the group consisting of methyl, ethyl, n-propyl, isopropyl, n-butyl, t-butyl, isobutyl, sec-butyl, 2-methyl-2-hexanyl, 1-methylcyclohexyl, cyclopropylmethyl, (cyclohexyl)methyl, isomers of n-pentyl, isomers of n-hexyl, isomers of n-heptyl, and isomers of n-octyl. More preferably, the aliphatic group is C1-C6 alkyl, and most preferably methyl. Substituted aliphatic groups are preferably substituted with methoxy or halide. The aryl group is preferably selected from the group consisting of phenyl, 1-naphthyl, 2-naphthyl and 4-biphenyl, most preferably phenyl. The substituted aryl group is preferably substituted with one or more substituents selected from the group consisting of R''', OR''', halogen, and NO$_2$, wherein each R''' is methyl. The arylalkyl group is preferably selected from the group consisting of benzyl and phenethyl. Substituted arylalkyl groups are preferably substituted with one or more substituents selected from the group consisting of R''', OR''', halogen and NO$_2$, wherein each R''' is methyl.

In one embodiment of the present invention, a process is provided for the preparation of the compound of Formula (5):

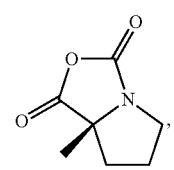

(5)

comprising reaction, in the presence of a solvent (S1), of the compound of Formula (6):

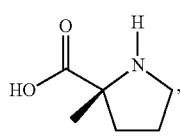

with a carbonylating agent.

The carbonylating agent may be any suitable reagent capable of undergoing attack by the carboxylic acid and amine functions of the compound of Formula (6) to thereby provide the required NCA derivative. This carbonylating agent is typically a carbonyl group bearing two substituents that function as leaving groups in the reaction with the compound of Formula (6) to provide the compound of Formula (5).

Preferably, the carbonylating agent is a compound of Formula (7):

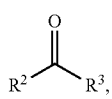

wherein $R^2$ and $R^3$ are independently selected from the group consisting of X, $OR^4$, $OCX_3$, imidazol-1-yl, 2-methylimidazol-1-yl and N-hydroxysuccinimidyl; X is halide; and $R^4$ is selected from the group consisting of alkyl, substituted alkyl, aryl and substituted aryl. $R^2$ and $R^3$ may be the same or different. The alkyl is preferably C1-C6 alkyl, more preferably methyl. The substituted alkyl is preferably C1-C6 alkyl, more preferably methyl substituted by halide. The aryl is preferably C6-C12 aryl, preferably phenyl. The substituted aryl is preferably C6-C12 substituted aryl, preferably substituted by nitro, halide or alkyloxy. Halide X is preferably chloride. Preferably, both $R^2$ and $R^3$ of the carbonylating agent (7) are the same, and are selected from the group consisting of chloride, $OCCl_3$, imidazol-1-yl and N-hydroxysuccinimidyl, corresponding with the following respective reagents: phosgene, triphosgene, carbonyldiimidazole (CDI) and N,N'-disuccinimidyl carbonate (DSC). Most preferably, the carbonylating agent (7) is carbonyldiimidazole.

When the carbonylating agent (7) is carbonyldiimidazole, reaction with the compound of Formula (6) is preferably conducted in the presence of imidazole hydrochloride, which acts as a catalyst for the reaction.

When conducting the reaction in the presence of a carbonylating agent (7) which yields an acid as a by-product (for example, when the carbonylating agent (7) is phosgene or triphosgene), a non-nucleophilic base (B1) is preferably used to neutralize this by-product. Base (B1) is preferably selected from the group consisting of tertiary amines, metal carbonates and metal bicarbonates, and more preferably, from metal carbonates and metal bicarbonates. More preferably, base (B1) is selected from the group consisting of sodium carbonate, sodium bicarbonate, potassium carbonate, potassium bicarbonate, lithium carbonate, triethylamine and diisopropylethylamine. Most preferably, base (B1) is sodium carbonate.

The reaction of the compound of Formula (6) and the carbonylating agent is conducted in the presence of a solvent (S1). Solvent (S1) is preferably selected from the group consisting of halogenated hydrocarbons, alkyl esters, ethers, nitriles and formamides. More preferably, solvent (S1) is selected from the group consisting of dichloromethane, ethyl acetate, tetrahydrofuran, acetonitrile and N,N-dimethylformamide. Most preferably, solvent (S1) is dichloromethane.

The reaction of the compound of Formula (6) and the carbonylating agent may be conducted at any suitable temperature, and is preferably conducted at a temperature between about −5° C. to about 20° C., and more preferably between about 0° C. to about 5° C.

The compound of Formula (6) is a commercially available substance, which may also be prepared by any desired method including, for example, Beck, A. K. et al. *Org. Synth.* 1995, 72, 62.

As illustrated in the following examples, use of the process described herein for the preparation of the compound of Formula (5) provides an increase in yield when compared to the corresponding reaction in Overberger et al. For example, in the following examples, yields as high as 81% can be obtained depending on the conditions used. In contrast, a yield of only 25% was achieved in the corresponding reaction for the preparation of the compound of Formula (5) in Overberger et al.

In another embodiment of the present invention, there is provided a process for the preparation of a compound of Formula (3):

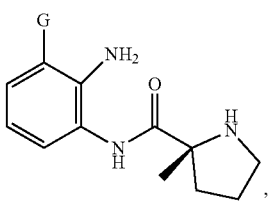

or a salt thereof, comprising coupling, in the presence of a solvent (S2), of the compound of Formula (5):

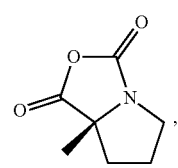

with a compound of Formula (4):

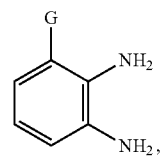

or a salt thereof,
wherein
G is $CONH_2$ or R;
R is $CO_2R^1$ or CN; and
$R^1$ is selected from the group consisting of H, an aliphatic group, a substituted aliphatic group, aryl, substituted aryl, arylalkyl and substituted arylalkyl.
Preferably, G is $CONH_2$ or $CO_2Me$.

The coupling of the compound of Formula (4) and the compound of Formula (5) is conducted in the presence of a solvent (S2). Solvent (S2) is preferably selected from the group consisting of halogenated hydrocarbons, ethers, nitriles and amides. More preferably, solvent (S2) is selected from the group consisting of dichloromethane, 1,4-dioxane, tetrahydrofuran, acetonitrile, N,N-dimethylformamide and N-methyl-2-pyrrolidone. Even more preferably, solvent (S2) is selected from the group consisting of 1,4-dioxane, tetrahydrofuran, N,N-dimethylformamide and N-methyl-2-pyrrolidone. Most preferably, solvent (S2) is tetrahydrofuran.

When an acid salt of the compound of Formula (4), such as the dihydrochloride salt, is used in the coupling with the compound of Formula (5), a base (B2-A) may be used to liberate the free amine. Base (B2-A) may be any suitable base capable of liberating the free form of the salt of Formula (4) and, is preferably selected from the group consisting of carbonates and tertiary amines.

Preferably, a base (B2-B) is used to facilitate the coupling of the compound of Formula (4) and the compound of Formula (5). Base (B2-B) is a non-nucleophilic base, preferably selected from the group consisting of alkyllithium bases, metal alkoxides, metal amides, metal hydrides, metal silyl amides, amidines and heteroaromatic amines. More preferably, base (B2-B) is selected from the group consisting of butyllithium, potassium t-butoxide, lithium diisopropylamide (LDA), sodium hydride, alkali metal hexamethyldisilazide, 1,8-diazabicyclo[5.4.0]undec-7-ene (DBU), 1-methylimidazole and 4-(dimethylamino)pyridine (DMAP). Most preferably, base (B2) is 1-methylimidazole or 4-(dimethylamino)pyridine (DMAP).

The coupling of the compound of Formula (4) and the compound of Formula (5) is typically conducted at an elevated temperature. However, higher temperatures can also lead to dimerization and inactivation of the compound of Formula (5) in the form of the compound of Formula (5'):

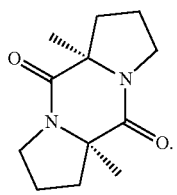

(5')

As such, a balance between promoting generation of the product and minimizing inactivation of the reactant of Formula (5) by dimerization is preferred. Subject to the particular combination of reagents and solvents, preferably a temperature of at least 50° C. is maintained and, in some cases, a temperature as high as 120° C. may be appropriate.

Compounds of Formula (4), and salts thereof, are commercially available substances and may also be prepared by any desired method, including, for example, the processes described in WO 2006/110816 A2 (compound of Formula (4-A) wherein G=CONH$_2$), CN 103755595 A (compound of Formula (4-BA) wherein G=CO$_2$R$^1$) and WO 2011/012622 A1 (compound of Formula (4-BC) wherein G=CN).

In another embodiment of the present invention, there is provided a process for the preparation of Veliparib (1):

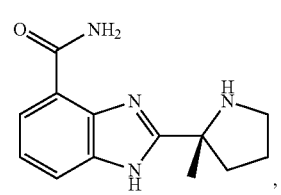

(1)

or a salt thereof, comprising
  (i) cyclization, in the presence of an acid (A1), of a compound of Formula (3):

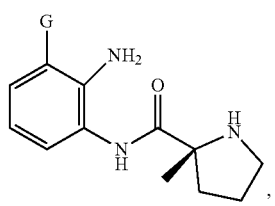

(3)

wherein
  G is CONH$_2$ or R;
to provide either Veliparib (1) when G is CONH$_2$ or, when G is R, a compound of Formula (2):

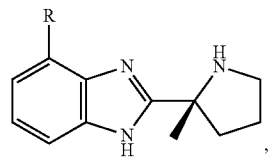

(2)

wherein
  R is CO$_2$R$^1$ or CN; and
  R$^1$ is selected from the group consisting of H, an aliphatic group, a substituted aliphatic group, aryl, substituted aryl, arylalkyl and substituted arylalkyl; and
  (ii) when G is R, conversion of the compound of Formula (2) to Veliparib (1).

Acid (A1) may be any suitable acid. Preferably, acid (A1) is selected from the group consisting of carboxylic acids, sulfonic acids and inorganic acids. More preferably, acid (A1) is selected from the group consisting of formic acid, acetic acid, p-toluene sulfonic acid, sulfuric acid and hydrochloric acid. Most preferably, acid (A1) is acetic acid.

In the cyclization of the compound of Formula (3), acid (A1) may function as solvent, or an additional solvent (S3) may be used. Solvent (S3) is selected from the group consisting of chlorinated hydrocarbons, aromatic hydrocarbons, ethers, nitriles, amides, alcohols and sulfoxides. Preferably, solvent (S3) is selected from the group consisting of dichloromethane, toluene, 1,4-dioxane, tetrahydrofuran, acetonitrile, N,N-dimethylformamide, N-methyl-2-pyrrolidone dimethylacetamide, methanol and dimethyl sulfoxide. Most preferably, acid (A1) is used as solvent.

The cyclization of the compound of Formula (3) may be conducted at any suitable temperature, preferably in the range of about room temperature to the boiling point of the reaction mixture. More preferably, the temperature is in the range of about room temperature to about 120° C. Most preferably, the temperature is in the range of about 100° C. to about 120° C.

Step (ii) is conducted when A in the compound of Formula (3) is R, corresponding with a compound of Formula (3-B):

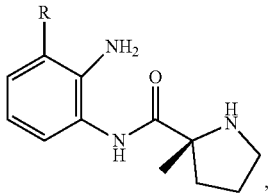

(3-B)

and the product of step (i) is a compound of Formula (2)

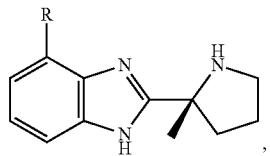

(2)

wherein
R is $CO_2R^1$ or CN; and
$R^1$ is selected from the group consisting of H, an aliphatic group, a substituted aliphatic group, aryl, substituted aryl, arylalkyl and substituted arylalkyl.

When R is $CO_2R^1$ and $R^1$ is H, the compound of Formula (2) is the compound of Formula (2-A):

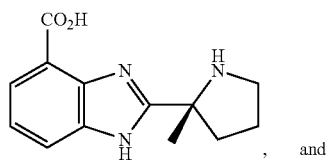

(2-A)

and step (ii) comprises conversion of the compound of Formula (2-A) to Veliparib (1).

Conversion of the compound of Formula (2-A) to Veliparib (1) preferably comprises treatment of the compound of Formula (2-A) with an agent to activate the carboxylic acid, followed by treatment with a source of ammonia. Preferably, the activating agent is a chlorinating agent. The chlorinating agent is preferably selected from the group consisting of thionyl chloride, oxalyl chloride, phosgene, triphosgene, phosphorous trichloride and phosphorous pentachloride. Most preferably, the chlorinating agent is thionyl chloride or oxalyl chloride.

The source of ammonia is preferably selected from the group consisting of ammonia gas, ammonium hydroxide and a solution of ammonia in an alcoholic solvent. Most preferably, the source of ammonia is a solution of ammonia in methanol solvent (methanolic ammonia).

The conversion of the compound of Formula (2-A) to the Veliparib (1) is preferably conducted in a solvent (S4) selected from the group consisting of halogenated hydrocarbons and ethers. More preferably, solvent (S4) is dichloromethane or tetrahydrofuran.

When R is $CO_2R^1$ and $R^1$ is not H, the compound of Formula (2) is a compound of Formula (2-B):

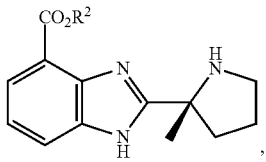

(2-B)

wherein $R^2$ is selected from the group consisting of an aliphatic group, a substituted aliphatic group, aryl, substituted aryl, arylalkyl and substituted arylalkyl, and step (ii) comprises conversion of the compound of Formula (2-B) to Veliparib (1).

Conversion of the compound of Formula (2-B) to Veliparib (1) preferably comprises treatment of the compound of Formula (2-B) with a source of ammonia. The source of ammonia is preferably selected from the group consisting of ammonia gas, ammonium hydroxide and a solution of ammonia in an alcoholic solvent. Most preferably, the source of ammonia is a solution of ammonia in methanol solvent (methanolic ammonia).

The conversion of the compound of Formula (2-B) to Veliparib (1) is preferably conducted in a solvent (S5) selected from the group consisting of water and alcohols. Most preferably, the ammonia source is used as solvent. Preferably, the conversion of the compound of Formula (2-B) to Veliparib (1) is conducted in a closed system under conditions of elevated temperature and pressure.

When R is ON, the compound of Formula (2) is the compound of Formula (2-C):

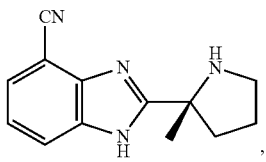

(2-C)

and step (ii) comprises conversion of the compound of Formula (2-C) to Veliparib (1).

Conversion of the compound of Formula (2-C) to Veliparib (1) preferably comprises hydrolysis of the compound of Formula (2-C) in the presence of an acid (A2) or a base (B3). When an acid (A2) is used for hydrolysis, it is preferably selected from the group consisting of mixtures of a mineral acid such as sulfuric acid or hydrochloric acid with an organic acid such as acetic acid or trifluoroacetic acid. Preferably, acid (A2) is a mixture of sulfuric acid and acetic acid, or a mixture of sulfuric acid and trifluoroacetic acid, and is preferably conducted in a substantially anhydrous system followed by quenching into water. Preferably, acid (A2) is also used as the solvent for hydrolysis.

When a base (B3) is used for hydrolysis, it is preferably an alkali metal hydroxide or an alkali metal alkoxide. Base (B3) may also be combined with hydrogen peroxide. Preferably, base (B3) is potassium t-butoxide. Base hydrolysis is preferably conducted in the presence of a solvent (S6) selected from the group consisting of alcohols and ethers. More preferably, solvent (S6) is t-butanol.

In another embodiment of the present invention, there is provided a process for the preparation of Veliparib (1):

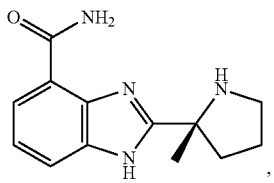

or a salt thereof, from a compound of Formula (2):

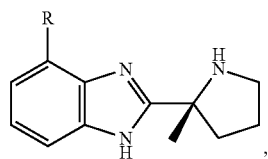

or a salt thereof, wherein
R is $CO_2R^1$ or CN; and
$R^1$ is selected from the group consisting of H, an aliphatic group, a substituted aliphatic group, aryl, substituted aryl, arylalkyl and substituted arylalkyl,
the process comprising:
(i) when R is $CO_2R^1$ and $R^1$ is H, treatment of the compound of Formula (2) with a chlorinating agent to activate the carboxylic acid followed by amidation with a source of ammonia;
(ii) when R is $CO_2R^1$ and $R^1$ is selected from the group consisting of an aliphatic group, a substituted aliphatic group, aryl, substituted aryl, arylalkyl and substituted arylalkyl, amidation of the compound of Formula (2) with a source of ammonia; or
(iii) when R is CN, hydrolysis of the compound of Formula (2) in the presence of an acid (A2) or a base (B3).

In the process for preparation of Veliparib (1), each of options (i), (ii) and (iii) may be conducted as described herein above.

In a preferred embodiment of the process of the present invention, the coupling of the compound of Formula (4) and the compound of Formula (5) to provide the compound of Formula (3), and the subsequent cyclization of the compound of Formula (3) to provide the compound of Formula (2) or Veliparib (1) is combined in a 'one-pot' approach. In this 'one-pot' approach, the coupling step is performed in the presence of acid (A1), which facilitates spontaneous cyclization of the compound of Formula (3) as it is formed to the compound of Formula (2) or Veliparib (1). In this approach, a base (B2-B) is not used for the coupling step, and the compound of Formula (3) is not isolated. Preferably, when acid (A1) is liquid, it is used as the solvent for both the coupling and cyclization reactions. Alternatively, a solvent chosen from solvent (S2) and/or solvent (S3) may be used. Acid (A1) may be any suitable acid as described herein, and for this approach is preferably substantially anhydrous and selected from the group consisting of carboxylic acids, sulfonic acids and inorganic acids. More preferably, acid (A1) is substantially anhydrous and selected from the group consisting of formic acid, acetic acid, p-toluene sulfonic acid, sulfuric acid and hydrochloric acid. Most preferably, acid (A1) is substantially anhydrous acetic acid (glacial acetic acid). In this approach, any suitable temperature may be used, preferably in the range of about room temperature to the boiling point of the reaction mixture. More preferably, the temperature is elevated above room temperature. Most preferably, the temperature is at least about 50° C.

In another embodiment of the present invention, there is provided a compound of Formula (3):

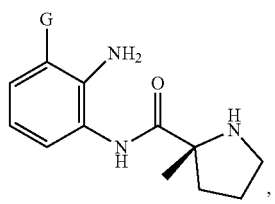

or a salt thereof, wherein
G is $CONH_2$ or R;
R is $CO_2R^1$ or CN; and
$R^1$ is selected from the group consisting of H, an aliphatic group, a substituted aliphatic group, aryl, substituted aryl, arylalkyl and substituted arylalkyl.

In the compound of Formula (3), or a salt thereof, the aliphatic group is preferably selected from the group consisting of methyl, ethyl, n-propyl, isopropyl, n-butyl, t-butyl, isobutyl, sec-butyl, 2-methyl-2-hexanyl, 1-methylcyclohexyl, cyclopropylmethyl, (cyclohexyl)methyl, isomers of n-pentyl, isomers of n-hexyl, isomers of n-heptyl, and isomers of n-octyl. More preferably, the aliphatic group is C1-C6 alkyl, and most preferably methyl. Substituted aliphatic groups are preferably substituted with methoxy or halide. The aryl group is preferably selected from the group consisting of phenyl, 1-naphthyl, 2-naphthyl and 4-biphenyl, most preferably phenyl. The substituted aryl group is preferably substituted with one or more substituents selected from the group consisting of R''', OR''', halogen, and $NO_2$, wherein each R''' is methyl. The arylalkyl group is preferably selected from the group consisting of benzyl and phenethyl. Substituted arylalkyl groups are preferably substituted with one or more substituents selected from the group consisting of R''', OR''', halogen and $NO_2$, wherein each R''' is methyl.

In the compound of Formula (3), or a salt thereof, G is preferably $CONH_2$ or $CO_2R^1$, wherein $R^1$ is C1-C6 alkyl, most preferably G is $CONH_2$ or $CO_2Me$. Most preferably, the compound of Formula (3) is the compound of Formula (3-A):

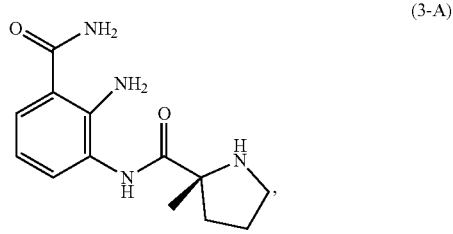 [SMILES: C[C@]1(C(=O)Nc2cccc(C(N)=O)c2N)CCCN1]

or a salt thereof, or the compound of Formula (3-BA1):

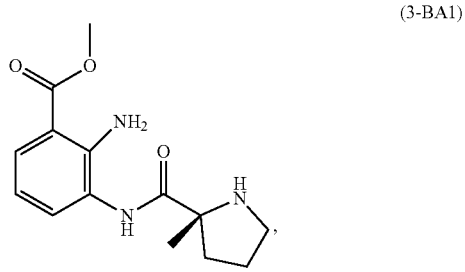 [SMILES: COC(=O)c1cccc(NC(=O)[C@@]2(C)CCCN2)c1N]

(3-BA1)

or a salt thereof.

In another embodiment of the present invention, there is provided a compound of Formula (2):

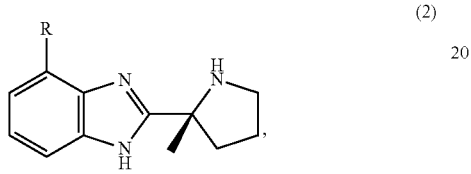

(2)

or a salt thereof,
wherein
R is $CO_2R^1$ or CN; and
$R^1$ is selected from the group consisting of H, a C2-C10 aliphatic group, a C1-C10 substituted aliphatic group, aryl, substituted aryl, arylalkyl and substituted arylalkyl.

In the compound of Formula (2), or a salt thereof, the aliphatic group is preferably selected from the group consisting of ethyl, n-propyl, isopropyl, n-butyl, t-butyl, isobutyl, sec-butyl, 2-methyl-2-hexanyl, 1-methylcyclohexyl, cyclopropylmethyl, (cyclohexyl)methyl, isomers of n-pentyl, isomers of n-hexyl, isomers of n-heptyl, and isomers of n-octyl. More preferably, the aliphatic group is C2-C6 alkyl, and most preferably ethyl. Substituted aliphatic groups are preferably substituted with methoxy or halide. The aryl group is preferably selected from the group consisting of phenyl, 1-naphthyl, 2-naphthyl and 4-biphenyl, most preferably phenyl. The substituted aryl group is preferably substituted with one or more substituents selected from the group consisting of R''', OR''', halogen, and $NO_2$, wherein each R''' is methyl. The arylalkyl group is preferably selected from the group consisting of benzyl and phenethyl. Substituted arylalkyl groups are preferably substituted with one or more substituents selected from the group consisting of R''', OR''', halogen and $NO_2$, wherein each R''' is methyl.

In the compound of Formula (2), or a salt thereof, R is preferably $CO_2R^1$ and $R^1$ is C2-C6 alkyl.

In another embodiment of the present invention, there is provided the diacetic acid salt of Veliparib (1):

EXAMPLES

The following examples are illustrative of some of the embodiments of the invention described herein. It will be apparent to the person skilled in the art that various alterations to the described processes in respect of the reactants, reagents and conditions may be made when using the processes of the present invention without departing from the scope or intent thereof.

Example 1: Preparation of (7aR)-7a-methyltetrahydro-1H,3H-pyrrolo[1,2-c][1,3]oxazole-1,3-dione (Compound of Formula (5)) Using CDI as Carbonylating Agent

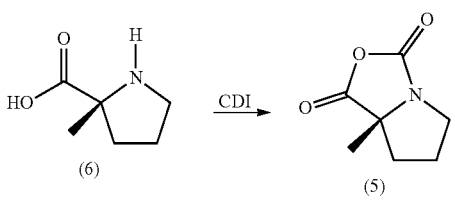

Carbonyldiimidazole (99%, 19.02 g, 116.14 mmol) was charged to a suspension of the compound of Formula (6) (5.0 g, 38.71 mmol), imidazole hydrochloride (12.95 g, 123.88 mmol), and dichloromethane (100 mL) at 0-5° C. After stirring at 0-5° C. for 3.5 hours, the reaction was deemed complete by $^1$H-NMR analysis (an aliquot was concentrated to dryness and dissolved in $CDCl_3$ to show complete consumption of the compound of Formula (6)), and was comprised of the compound of Formula (5) and the dimer of Formula (5') in a molar ratio of 96:4. The reaction suspension was filtered under a nitrogen stream to remove imidazole by-products, and the filter cake was washed with cold (0-5° C.) dichloromethane (10 mL). The filtrate was washed with a solution (5 wt %) of aqueous citric acid (2×50 mL) where the evolution of gas was observed. The organic layer was then separated, dried over anhydrous sodium sulfate, and concentrated in vacuo at 30-35° C. to afford the compound of Formula (5) as a white solid (4.89 g, 81% yield).

$^1$H-NMR compound of Formula (5): ($CDCl_3$, 300 MHz) δ: 1.54 (3H, s), 1.92-2.13 (2H, m), 2.15-2.27 (2H, m), 3.34 (1H, ddd, J=6.9 Hz, 6.9 Hz, 11.8 Hz), 3.83 (1H, ddd, J=7.7 Hz, 7.7 Hz, 11.5 Hz). $^1$H-NMR compound of Formula (5'): ($CDCl_3$, 300 MHz) δ: 1.51 (6H, s), 1.94-2.18 (8H, m), 3.43-3.55 (2H, m), 3.72-3.85 (2H, m).

Example 2: Preparation of N-(2-amino-3-carbamoylphenyl)-2-methyl-D-prolinamide (Compound of Formula (3-A))

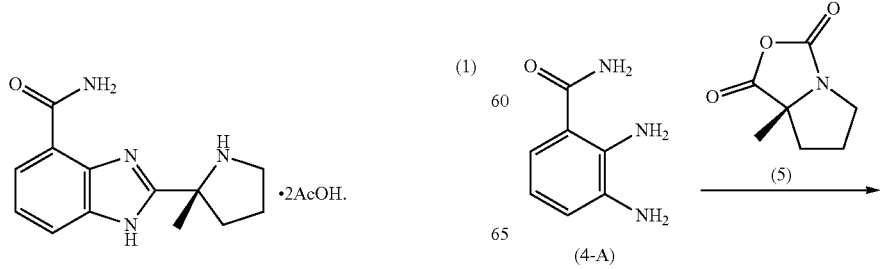

-continued

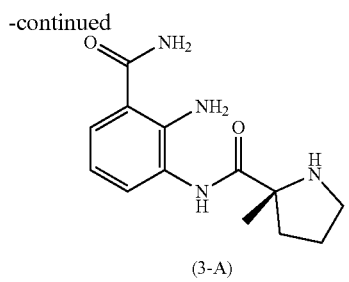

(3-A)

The compound of Formula (5) (500 mg, 3.22 mmol) was charged portion-wise over one hour to a clear, light brown solution of the compound of Formula (4-A) (240 mg, 1.60 mmol) and 1-methylimidazole (13 mg, 0.16 mmol) in tetrahydrofuran (3 mL) at reflux (67° C.). The reaction was heated at reflux and the progress monitored by $^1$H-NMR (an aliquot was concentrated to dryness and dissolved in CDCl$_3$). After 21 hours, the reaction showed no further progression (approximately 53 mole % of Formula (4-A) had converted to Formula (3-A)), and the mixture was allowed to reach room temperature and concentrated to dryness in vacuo to afford a dark residue (1.0 g). The crude solid was purified by column chromatography (10-20% methanol in ethyl acetate) to afford the compound of Formula (3-A) as a yellow residue (95 mg, 23% yield).

$^1$H-NMR (DMSO-d$_6$, 300 MHz) δ: 1.37 (3H, s), 1.49-1.80 (3H, m), 2.14 (1H, ddd, J=5.2 Hz, 6.8 Hz, 12.0 Hz), 2.78-2.92 (2H, m), 2.98-3.10 (1H, m), 6.07 (2H, s), 6.60 (1H, t, J=7.8 Hz), 7.21 (1H, broad s), 7.42 (1H, dd, J=1.2 Hz, 7.9 Hz), 7.49 (1H, dd, J=1.1 Hz, 7.8 Hz), 7.85 (1H, broad s), 9.80 (1H, s).

Example 3: Preparation of methyl 2-amino-3-[(2-methyl-D-prolyl)amino]benzoate (Compound of Formula (3-BA1))

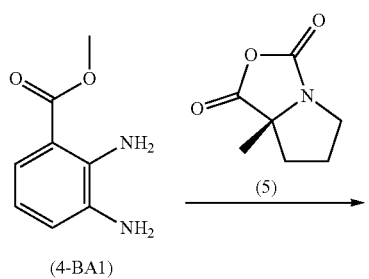

A dark brown solution of the compound of Formula (4-BA1) (0.54 g, 3.2 mmol) and the compound of Formula (5) (0.50 g, 3.2 mmol) in anhydrous tetrahydrofuran (12 mL) was cooled to −50° C. Sodium bis(trimethylsilyl)amide (1 M in THF, 9.6 mL) was added dropwise maintaining the internal temperature below −40° C. Upon complete addition, the reaction mixture was maintained in the cold for 2 hours and warmed to 0-5° C. for 1 hour at which point negligible amounts of the compound of Formula (4-BA1) remained as determined by $^1$H NMR (an aliquot was added to a mixture of aqueous ammonium chloride and dichloromethane, the organic phase was concentrated to dryness and dissolved in DMSO-d$^6$). The reaction mixture was warmed to room temperature and aqueous ammonium chloride was added (30 mL) and the mixture was concentrated in vacuo to remove the tetrahydrofuran. Dichloromethane (30 mL) was added to the biphasic mixture and the phases separated. The aqueous phase was extracted with dichloromethane (15 mL) and the combined organic phases were washed with water (15 mL), dried over anhydrous sodium sulfate and concentrated to dryness affording a brown residue (0.67 g). The residue was purified by column chromatography (10% methanol in ethyl acetate) to afford the compound of Formula (3-BA1) (0.15 g) as well as the corresponding regioisomer (compound of Formula (3-BA1')):

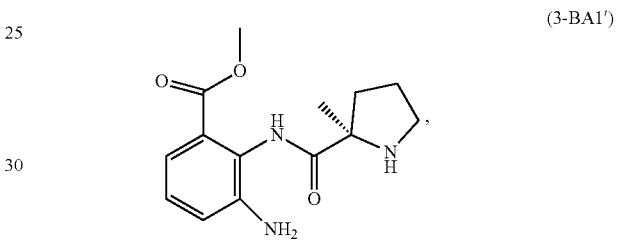

(3-BA1')

(0.06 g), both of which are suitable for the production of the compound of Formula (2-A1) according to the procedure given in Example 5.

$^1$H-NMR compound of Formula (3-BA1): (DMSO-d$_6$, 300 MHz) δ: 1.38 (3H, s), 1.49-1.62 (1H, m), 1.62-1.81 (2H, m), 2.15 (1H, ddd, J=5.3 Hz, 6.7 Hz, 12.1 Hz), 2.76-2.92 (2H, m), 3.04 (1H, ddd, J=6.8 Hz, 6.8 Hz, 10.1 Hz), 3.81 (3H, s), 6.16 (2H, s), 6.64 (1H, t, J=7.9 Hz), 7.52 (1H, dd, J=1.4 Hz, 7.7 Hz), 7.63 (1H, dd, J=1.5 Hz, 8.1 Hz), 9.81 (1H, s).

$^1$H-NMR compound of Formula (3-BA1'): (DMSO-d$_6$, 300 MHz) δ: 1.36 (3H, s), 1.48-1.60 (1H, m), 1.60-1.76 (2H, m), 2.12 (1H, ddd, J=5.3 Hz, 7.0 Hz, 12.1 Hz), 2.75-2.95 (2H, m), 2.95-3.10 (1H, m), 3.75 (3H, s), 4.89 (2H, s), 6.97-7.10 (3H, m), 10.45 (1H, s).

Example 4: Preparation of methyl 2-amino-3-[(2-methyl-D-prolyl)amino]benzoate (Compound of Formula (3-BA1))

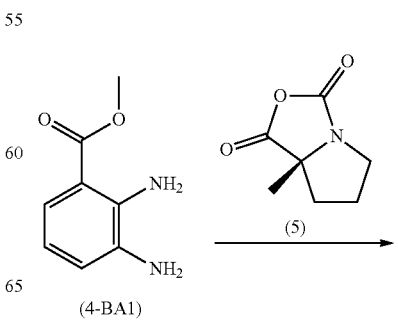

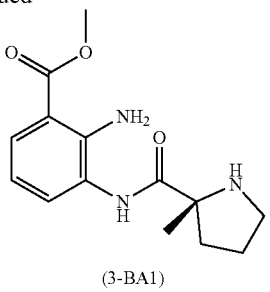

(3-BA1)

A dark brown solution of the compound of Formula (4-BA1) (2.14 g, 12.89 mmol), the compound of Formula (5) (2.00 g, 12.89 mmol), 4-(dimethylamino)pyridine (0.32 g, 2.58 mmol) and anhydrous tetrahydrofuran (40 mL) was heated to reflux at 67° C. After 2 hours of heating, a second portion of 4-(dimethylamino)pyridine (0.32 g, 2.58 mmol) was charged to the reaction and effervescence was observed. After an additional 4.5 hours of heating, $^1$H NMR analysis (an aliquot was concentrated to dryness and dissolved in CDCl$_3$) showed no further progression so the reaction mixture was cooled to room temperature and concentrated in vacuo at 30-35° C. to afford a dark residue (4.39 g). The residue was then purified by column chromatography (10-20% methanol in ethyl acetate) to afford the compound of Formula (3-BA1) as a brown solid (0.75 g, 2.69 mmol).

Example 5: Preparation of methyl 2-[(2R)-2-methylpyrrolidin-2-yl]-1H-benzimidazole-4-carboxylate (Compound of Formula (2-B1) from the Compound of Formula (3-BA1))

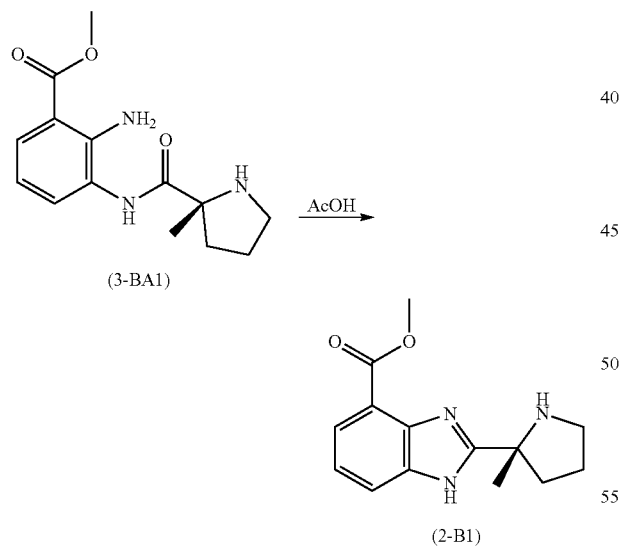

The compound of Formula (3-BA1) (0.20 g, 0.72 mmol) and glacial acetic acid (2 mL) were combined in a flask and heated to reflux at 118° C. affording a dark, clear solution. The reaction was deemed complete after 2 hours by thin-layer chromatography (TLC) (1:9 methanol: ethyl acetate, Formula (3-BA1) R$_f$=0.25, Formula (2-A1) R$_f$=0.14). The reaction mixture was cooled to room temperature and concentrated in vacuo at 35-40° C. to remove the acetic acid. The residue was dissolved in ethyl acetate (3 mL) and washed with aqueous saturated sodium bicarbonate solution (3 mL). The organic layer was then separated, dried over anhydrous sodium sulfate, and concentrated in vacuo at 30-35° C. to afford a residue (0.16 g). The residue (0.16 g) was dissolved in 4% hydrochloric acid (3 mL) and was washed with ethyl acetate (2×3 mL). The acidic aqueous layer was basified to a pH of 6-7 using 50 wt % sodium hydroxide and was extracted with ethyl acetate (3 mL). The organic layer was then dried over anhydrous sodium sulfate and concentrated in vacuo at 30-35° C. to afford a residue (0.10 g). The residue was purified by column chromatography (20% methanol in ethyl acetate) to afford the compound of Formula (2-B1) as a clear oil (72 mg, 0.28 mmol).

$^1$H-NMR (DMSO-d$_6$, 300 MHz) δ: 1.54 (3H, s), 1.58-1.71 (1H, m), 1.72-1.89 (2H, m), 2.39-2.47 (1H, m), 2.74-2.86 (1H, m), 3.00-3.12 (1H, m), 3.95 (3H, s), 7.27 (1H, t, J=7.8 Hz), 7.77 (1H, dd, J=0.8 Hz, 7.7 Hz), 7.85 (1H, dd, J=0.7 Hz, 8.0 Hz).

Example 6: One-pot preparation of methyl 2-[(2R)-2-methylpyrrolidin-2-yl]-1H-benzimidazole-4-carboxylate (Compound of Formula (2-B1)) from the Compound of Formula (4-BA1)

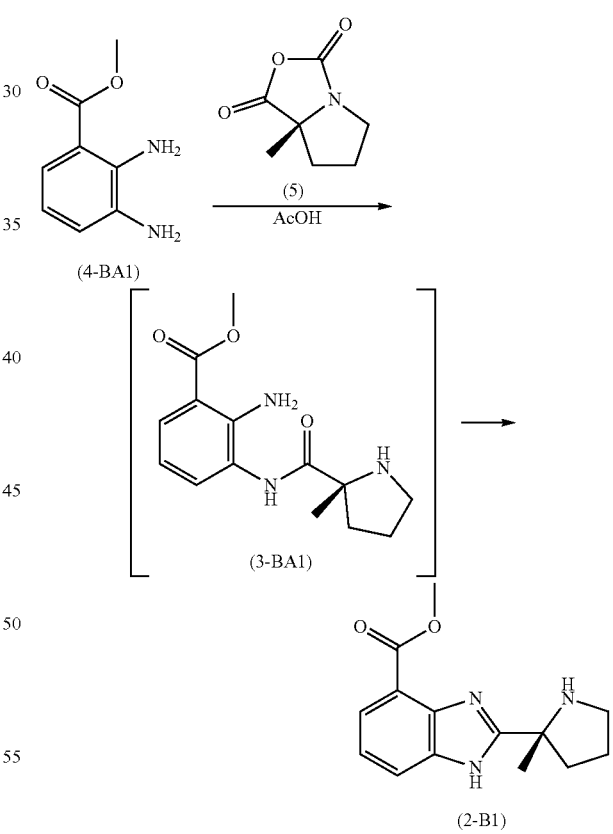

An NMR tube was charged with the compound of Formula (4-BA1) (20 mg, 0.12 mmol), the compound of Formula (5) (37 mg, 0.24 mmol) and deuterated acetic acid (d$^4$-AcOH, 1 mL) and sealed with a cap. The sealed tube was heated to an external temperature of 48° C. for 16 hours at which point the reaction was deemed complete by $^1$H-NMR (indicated by consumption of Formula (5) multiplet at 3.3-3.4 ppm). The $^1$H-NMR analysis also showed that the molar ratio of components bearing aromatic protons was approximately: 48:4:47 Formula (4-BA1): Formula (3-BA1): Formula (2-B1), indicating approximately 50% conversion.

Example 7: Preparation of Veliparib (1) as the Deuterated Diacetic Acid Salt from the Compound of Formula (3-A)

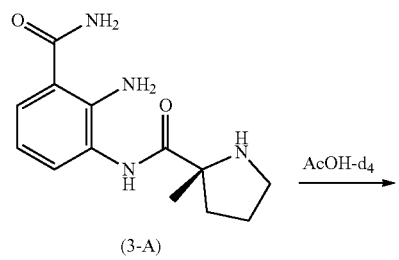
(3-A)

AcOH-d$_4$ →

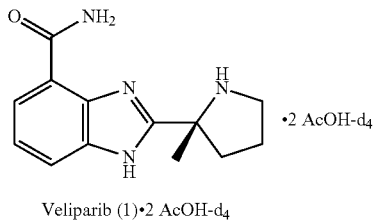
Veliparib (1)·2 AcOH-d$_4$

An NMR tube was charged with the compound of Formula (3-A) (11 mg, 0.04 mmol) and deuterated acetic acid (d$_4$-AcOH, 0.5 mL) and sealed with plastic paraffin wrap. The sealed tube was heated to an external temperature of 120° C. for 3 hours at which point the reaction was deemed complete by $^1$H-NMR (indicated by disappearance of Formula (3-A) multiplet at 2.6-2.8 ppm and appearance of new product multiplet at 2.8-2.9 ppm). The heating bath was cooled to 50° C. and a stream of nitrogen gas was applied to evaporate the AcOH-d$_4$ at which point a $^1$H-NMR in D$_2$O provided confirmation of Veliparib (1) as the diacetic acid-d$_4$ salt.

$^1$H-NMR (D$_2$O, 300 MHz) δ: 1.92 (3H, s), 1.96-2.14 (1H, m), 2.18-2.32 (1H, m), 2.32-2.44 (1H, m), 2.54 (1H, ddd, J=5.4 Hz, 8.1 Hz, 13.5 Hz), 3.52-3.68 (2H, m), 7.26 (1H, t, J=7.9 Hz), 7.63 (1H, dd, J=0.7 Hz, 8.1 Hz), 7.67 (1H, dd, J=0.8 Hz, 7.7 Hz).

Example 8: One-Pot Preparation of Veliparib (1) as the Deuterated Diacetic Acid Salt from the Compound of Formula (4-A)

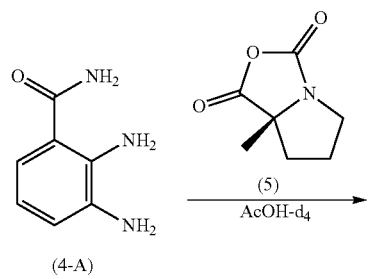
(4-A) (5) AcOH-d$_4$ →

-continued

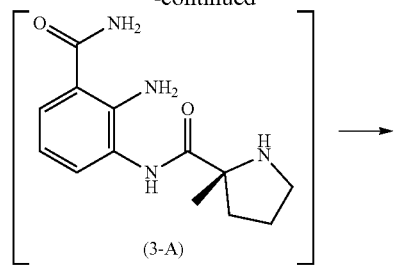
(3-A)

→

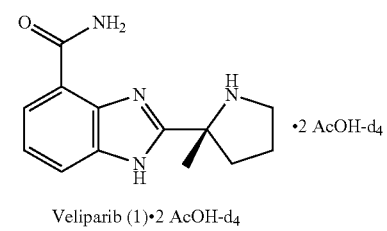
Veliparib (1)·2 AcOH-d$_4$

An NMR tube was charged with the compound of Formula (4-A) (20 mg, 0.13 mmol), the compound of Formula (5) (41 mg, 0.26 mmol) and deuterated acetic acid (0.6 mL) and sealed with plastic paraffin wrap. The sealed tube was heated to an external temperature of 48° C. for 15 hours at which point the reaction was deemed complete by $^1$H-NMR (indicated by consumption of Formula (5) multiplet at 3.3-3.4 ppm). The $^1$H-NMR analysis also showed that the molar ratio of components bearing aromatic protons was approximately: 17:4:79 Formula (4-A): Formula (3-A): Veliparib (1) 2AcOH-d$_4$, indicating approximately 80% conversion.

What is claimed is:

1. A process for preparing Veliparib (1):

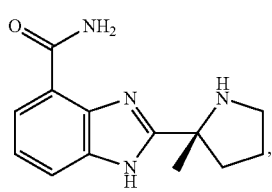
(1)

or a salt thereof, comprising
(i) cyclizing, in the presence of an acid (A1), a compound of Formula (3):

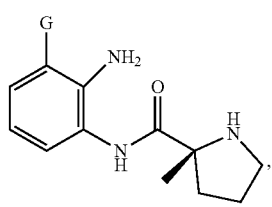
(3)

wherein
G is CONH₂ or R;
R is CO₂R¹ or CN; and
R¹ is selected from the group consisting of H, an aliphatic group, a substituted aliphatic group, aryl, substituted aryl, arylalkyl and substituted arylalkyl;
to provide either Veliparib (1) when G is CONH₂, or, when G is R, a compound of Formula (2):

(2)

and
wherein
R is CO₂R¹ or CN; and
R¹ is selected from the group consisting of H, an aliphatic group, a substituted aliphatic group, aryl, substituted aryl, arylalkyl and substituted arylalkyl; and
(ii) when G is R, converting the compound of Formula (2) to Veliparib (1).

2. The process of claim 1, wherein G is CONH₂.
3. The process of claim 1, wherein G is R, R is CO₂R¹, and R¹ is H.
4. The process of claim 1, wherein G is R, R is CO₂R¹, and R¹ is an aliphatic group.
5. The process of claim 4, wherein R¹ is C1-C6 alkyl.
6. The process of claim 5, wherein R¹ is methyl.
7. The process of claim 6, wherein in step (ii), converting of the compound of Formula (2) to Veliparib (1) comprises treating the compound of Formula (2) with a source of ammonia.
8. The process of claim 7, wherein the source of ammonia is selected from the group consisting of ammonia gas, ammonium hydroxide and a solution of ammonia in methanol solvent.
9. The process of claim 1, wherein acid (A1) is a substantially anhydrous acid selected from the group consisting of carboxylic acids, sulfonic acids and mineral acids.
10. The process of claim 9, wherein acid (A1) is acetic acid.
11. The process of claim 10, wherein G in the compound of Formula (3) is CONH₂, and Veliparib (1) is provided as a diacetic acid salt.
12. A process for the preparing a compound of Formula (3):

(3)

or a salt thereof, wherein
G is CONH₂ or R;
R is CO₂R¹ or CN; and
R¹ is selected from the group consisting of H, an aliphatic group, a substituted aliphatic group, aryl, substituted aryl, arylalkyl and substituted arylalkyl;
comprising coupling, in the presence of a solvent (S2), of the compound of Formula (5):

(5)

with a compound of Formula (4):

(4)

or a salt thereof,
wherein
G is CONH₂ or R;
R is CO₂R¹ or CN; and
R¹ is selected from the group consisting of H, an aliphatic group, a substituted aliphatic group, aryl, substituted aryl, arylalkyl and substituted arylalkyl.

13. The process of claim 12, wherein G is CONH₂.
14. The process of claim 13, wherein solvent (S2) is selected from the group consisting of 1,4-dioxane, tetrahydrofuran, N,N-dimethylformamide and N-methyl-2-pyrrolidone.
15. The process of claim 13, wherein the coupling is conducted at a temperature of at least about 50° C.
16. The process of claim 13, wherein the coupling is conducted in the presence of a base (B2-B) that is selected from the group consisting of 4-(dimethylamino)pyridine and 1-methylimidazole.
17. A compound of Formula (3):

(3)

or a salt thereof, wherein

G is CONH$_2$ or R;

R is CO$_2$R$^1$ or CN; and

R$^1$ is selected from the group consisting of H, an aliphatic group, a substituted aliphatic group, aryl, substituted aryl, arylalkyl and substituted arylalkyl.

18. The compound of claim 17, or a salt thereof, wherein G is CONH$_2$ or CO$_2$R$^1$ and R$^1$ is C1-C6 alkyl.

19. The compound of claim 17, having the Formula (3-A):

(3-A)

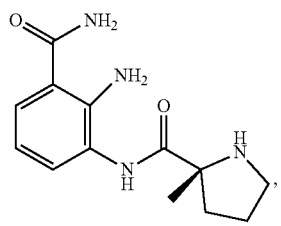

or a salt thereof, or having the Formula (3-BA1):

(3-BA1)

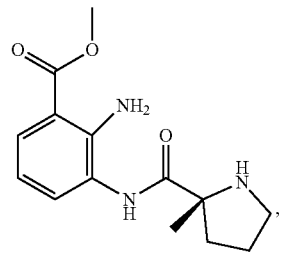

or a salt thereof.

20. The compound of claim 17, having the Formula (3-A):

(3-A)

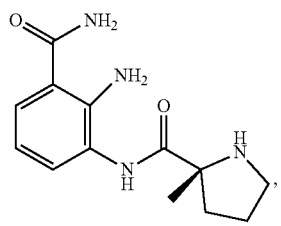

or a salt thereof.

* * * * *